United States Patent
Desgranges et al.

(10) Patent No.: US 10,285,578 B2
(45) Date of Patent: May 14, 2019

(54) DENTAL EXAM TOOL

(71) Applicants: Patrick Zana Desgranges, Wichita, KS (US); Philip Yaghmai, Wichita, KS (US); Bryce Gartner, Wichita, KS (US)

(72) Inventors: Patrick Zana Desgranges, Wichita, KS (US); Philip Yaghmai, Wichita, KS (US); Bryce Gartner, Wichita, KS (US)

(73) Assignee: VIGILIAS LLC, Wichita, KS (US)

( * ) Notice: Subject to any disclaimer, the term of this patent is extended or adjusted under 35 U.S.C. 154(b) by 0 days.

(21) Appl. No.: 15/694,489

(22) Filed: Sep. 1, 2017

(65) Prior Publication Data
US 2018/0064326 A1    Mar. 8, 2018

Related U.S. Application Data

(60) Provisional application No. 62/383,071, filed on Sep. 2, 2016.

(51) Int. Cl.
*A61B 1/00* (2006.01)
*A61B 1/247* (2006.01)
*A61B 1/04* (2006.01)

(52) U.S. Cl.
CPC .......... *A61B 1/247* (2013.01); *A61B 1/00128* (2013.01); *A61B 1/04* (2013.01)

(58) Field of Classification Search
CPC ........ A61B 1/247; A61B 1/00128; A61B 1/04
See application file for complete search history.

(56) References Cited

U.S. PATENT DOCUMENTS

| | | | | |
|---|---|---|---|---|
| 6,172,613 | B1* | 1/2001 | DeLine | B60K 35/00 248/549 |
| 9,585,549 | B1* | 3/2017 | Elazar | A61B 1/247 |
| 2005/0003323 | A1* | 1/2005 | Katsuda | A61B 1/00089 433/29 |
| 2006/0263030 | A1* | 11/2006 | Oh | H04M 1/21 385/147 |
| 2007/0066247 | A1* | 3/2007 | Mooney | H04M 1/21 455/90.3 |
| 2010/0195222 | A1* | 8/2010 | Eccher | A45D 33/26 359/804 |
| 2011/0294542 | A1* | 12/2011 | Ray | H04B 1/3888 455/556.1 |
| 2013/0135871 | A1* | 5/2013 | Harooni | A45C 15/04 362/268 |
| 2013/0183633 | A1* | 7/2013 | Dillon | A61B 1/00048 433/31 |

(Continued)

*Primary Examiner* — Nicholas D Lucchesi
(74) *Attorney, Agent, or Firm* — Schwabe Williamson & Wyatt, PC (57) ABSTRACT

Disclosed is a dental exam tool for attaching to a mobile electronic device. The dental exam tool can include a coupling element that securely and removably couples to a body portion of the mobile electronic device and a dental mirror retention element coupled to the coupling element. Also disclosed is a dental exam system for teledentistry. The dental exam system can include a dental exam tool for attaching to a mobile electronic device and a mobile electronic device, having a camera, wherein the mobile electronic device is capable of capturing still images and/or video from the camera and storing and/or transmitting the images and/or video captured.

20 Claims, 6 Drawing Sheets

(56) References Cited

U.S. PATENT DOCUMENTS

| | | | |
|---|---|---|---|
| 2013/0323671 A1* | 12/2013 | Dillon | A61B 6/145 |
| | | | 433/29 |
| 2013/0330684 A1* | 12/2013 | Dillon | A61B 1/00039 |
| | | | 433/29 |
| 2014/0049851 A1* | 2/2014 | Snell | F16M 11/041 |
| | | | 359/871 |
| 2014/0272766 A1* | 9/2014 | Andreiko | A61B 1/00048 |
| | | | 433/27 |
| 2015/0004557 A1* | 1/2015 | Hillebrandt | G06Q 50/22 |
| | | | 433/29 |
| 2015/0293877 A1* | 10/2015 | Liang | A61B 1/00016 |
| | | | 710/33 |
| 2017/0209033 A1* | 7/2017 | Yu | A61B 1/07 |
| 2017/0273539 A1* | 9/2017 | Law | A61B 1/00 |
| 2018/0125187 A1* | 5/2018 | Malavazos | A45F 4/04 |
| 2018/0125610 A1* | 5/2018 | Carrier, Jr. | A61C 7/002 |
| 2018/0220889 A1* | 8/2018 | Dirghangi | A61B 3/185 |

* cited by examiner

DENTAL EXAM TOOL

CROSS REFERENCE TO RELATED APPLICATION

This disclosure claims the benefit to U.S. Provisional Application No. 62/383,071, filed on Sep. 2, 2016, which is hereby incorporated by reference in its entirety.

TECHNICAL FIELD

Embodiments herein relate to the field of dentistry, and, more specifically a dental exam tool that attaches to a mobile electronic device, such as a smart phone.

BACKGROUND

Teledentistry is a subset of telemedicine that uses information technology and telecommunications for dental care and consultation. In some situations, teledentistry is used to assist general dentists with specialty work and improve services to underserved populations, such as in rural or less developed areas.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Figure 1:
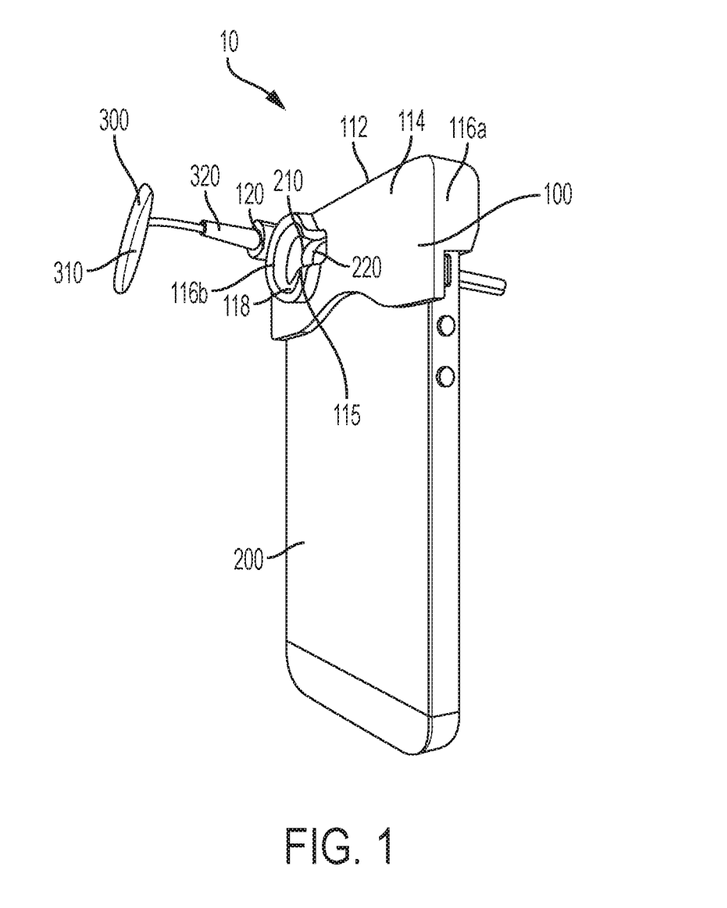
FIG. 1 is an exemplary dental exam system including a dental exam tool, in accordance with embodiments herein.
Figure 2:
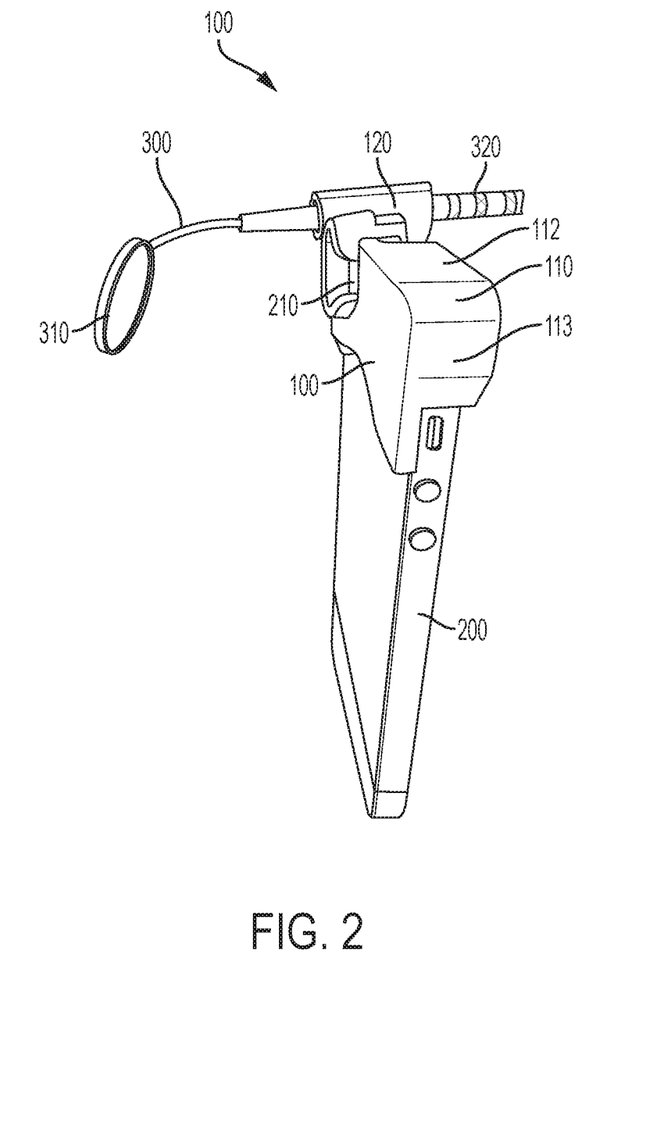
FIG. 2 is another view of the exemplary dental exam system including a dental exam tool shown in FIG. 1, in accordance with embodiments herein.

FIGS. 1 and 2 provide an exemplary mobile dental exam system 10, in accordance with embodiments herein. In the embodiment shown, the mobile dental exam system 10 includes a dental exam tool 100 and a mobile electronic device 200, which in the image shown is a smart phone, such as an iPhone®. Thus, in embodiments, the dental exam tool 100 is configured to reversibly attach to a mobile electronic device 200. In various embodiments, the mobile electronic device 200 is a hand held device, such as a cell phone, a smart phone, or a tablet. In certain embodiments, the mobile electronic device 200 is part of a larger device, such as a computing system, for example in wired or wireless communication with the computing system. In embodiments, the mobile electronic device 200 includes a camera 210. In embodiments, the mobile electronic device 200 is capable of capturing still images and/or video from the camera 210 and storing and/or transmitting the images and/or video captured. Thus, in some embodiments the mobile electronic device 200 includes a storage medium, such as a non-volatile storage medium. In some embodiments, the mobile electronic device 200 includes a transmitter, for example to transmit images and/or video captured by the camera 210, for example in real time or at a later time. In embodiments, the mobile electronic device 200 includes one or more processors, for example to carry out instruction for capturing video and/or images, storing, and/or transmitting those images and/or videos. In some embodiments, the mobile electronic device 200 includes one or more of a speaker, a microphone, and a video screen. In some embodiments, the mobile electronic device 200 includes a light source 220, for example to illuminate the mouth of a subject using the mobile dental exam system. In embodiments, the mobile dental exam system is in electronic communication with a third party computing device, for example wired or wireless communication. For example, a third party computing device that can be located in dental practitioner's office, such as a dental office. Thus, in some embodiments the mobile dental exam system includes a third party computing device.

The mobile dental exam system 10 includes a dental exam tool 100 for attaching to a mobile electronic device 200. In some embodiments, the dental exam tool 100 is separate from the mobile electronic device 200, such that it is obtained separate from the mobile electronic device 200 and applied or attached to different devices. In embodiments, the dental exam tool 100 includes a coupling element 110 that securely and removably couples to the mobile electronic device 200. In embodiments, the dental exam tool 100 includes a dental mirror retention element 120 that is coupled to the coupling element 110. In embodiments, the mobile dental exam system 10 includes a dental mirror 300, which is retained in position by the dental mirror retention element 120. In embodiments, the dental mirror retention element 120 positions a reflective portion 310 of the dental mirror 300 in front of a camera lens 210 of the mobile electronic device 200 or an auxiliary lens.

In embodiments, the dental exam tool 100 for attaching to a mobile electronic device includes a coupling element 110 that securely and removably couples to a body portion of the mobile electronic device 200. In embodiments, the coupling element 110 includes an aperture 115 for the camera lens 210 on the body portion of the mobile electronic device 200. In embodiments, the dental exam tool 100 includes a dental mirror retention element 120 coupled to the coupling element 110. In embodiments, the coupling element 110 includes an aperture for a light source 220 of the mobile electronic device 200. The aperture can be contiguous with the camera aperture 115 or discrete. In embodiments, the coupling element 110 and the dental mirror retention element 120 are a unitary body, for example composed of a single piece of material. In embodiments, the dental exam tool 200 is formed from plastic, such as autoclavable plastic, for example polypropylene, polymethylpentene, polycarbonate, polytetrafluoroethylene (PTFE), and polymethyl methacrylate. In embodiments, the dental mirror retention element is 120 is configured to retain a dental mirror 300 with a substantial cylindrical shaft 320. In embodiments, the dental mirror retention element 120 positions a reflective portion 310 of the dental mirror 300 in front of the camera lens 210 of the mobile electronic device 200. In embodiments, the dental exam tool 100 is configured to slide over the top of the mobile electronic device 200, for example such that a portion of the mobile electronic device nests within a cavity of the coupling element 110, which is formed from a top 112, a back 114, a front and sides 116a,116b of the coupling element 110. In some embodiment, the aperture 115 includes a lip 118 that extend from the back 114 of the coupling element 110. The lip 118 can act to shield the lens 210 of the mobile electronic device 200 from glare.

Figure 3:
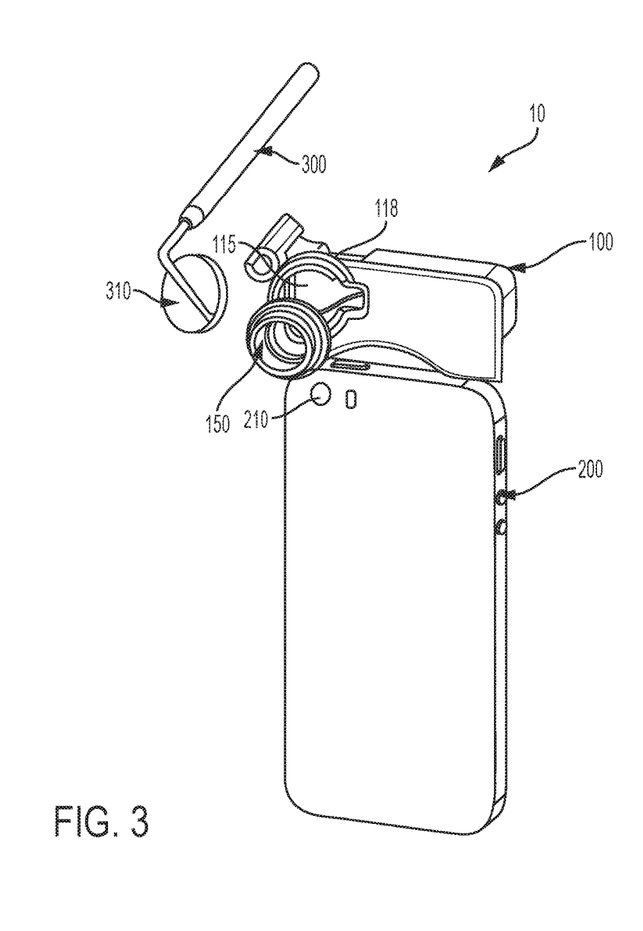
FIG. 3 includes two views of an exemplary dental exam system including a dental exam tool, in accordance with embodiments herein.

FIG. 3 provides a set of perspective views of an exemplary mobile dental exam system 10, in accordance with embodiments herein. In the embodiment shown, the mobile dental exam system 10 includes a dental exam tool 100, a mobile electronic device 200, and a dental mirror 300. In embodiments, the mobile electronic device 200 includes a camera 210. In embodiments, the dental exam tool 100 positions a reflective portion 310 of the dental mirror 300 in front of the camera lens 210 of the mobile electronic device 200. In embodiments, the coupling element 110 includes an aperture 115 for a camera lens 210 on the body portion of the mobile electronic device 200. In some embodiments, the aperture 115 includes a lip 118 that extend from the back 114 of the coupling element 110. In embodiments, the lip 118 is configured to reversibly couple to a lensing system 150 and position the lensing system 150 in front of the camera lens 210 and focus camera on the dental mirror 300 reflective portion 310. In embodiments, the lensing system 150 includes a magnifying lens, for example to enlarge the image reflected by dental mirror 300. In embodiments, the lensing system 150 has a range in magnification from about 1× magnification to about 10× magnification, such as 1×, 2×, 3×, 4×, 5×, 6×, 7×, 8×, 9×, or 10×, In embodiments, the magnification of the lensing system 150 is adjustable, for example between about 1× magnification and about 10× magnification.

Figure 4:
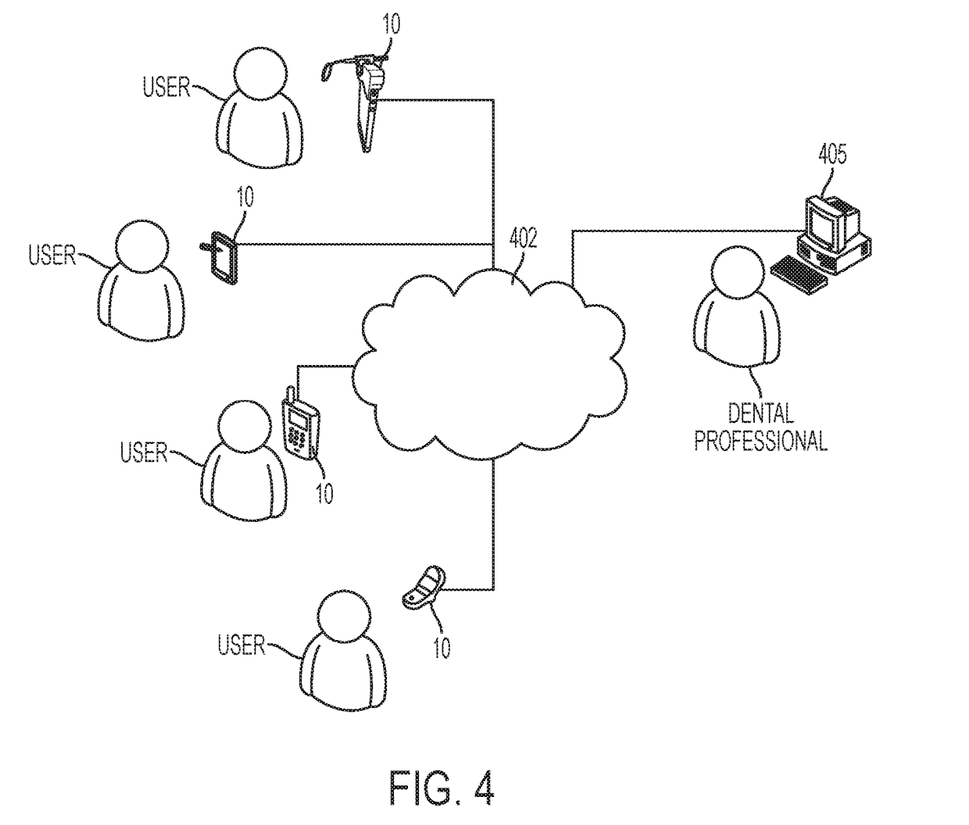
FIG. 4 is a schematic diagram of a teledentistry system using an exemplary dental exam tool, in accordance with embodiments herein.

FIG. 4 is a schematic diagram of a teledentistry 400 system using an exemplary dental exam system 10, in accordance with embodiments herein. As depicted in FIG. 4, the dental exam system 10 distributes information to one or more networked devices 405 through one or more of network 402. Each network 402 includes a wired or wireless telecommunication means by which network systems (including dental exam system 10 and networked devices 405) may communicate and exchange data. For example, each network 402 may be implemented as, or may be a part of, a storage area network (SAN), personal area network (PAN), a metropolitan area network (MAN), a local area network (LAN), a wide area network (WAN), a wireless local area network (WLAN), a virtual private network (VPN), an intranet, an Internet, a mobile telephone network, a card network, Bluetooth, near field communication network (NFC), any form of standardized radio frequency, or any combination thereof, or any other appropriate architecture or system that facilitates the communication of signals, data, and/or messages (generally referred to as data). Throughout this specification, it should be understood that the terms "data" and "information" are used interchangeably herein to refer to text, images, audio, video, or any other form of information that can exist in a computer-based environment.

In an exemplary embodiment, each network system (including dental exam system 10 and networked devices 405) includes a device having a communication component capable of transmitting and/or receiving data over the network 402. For example, each networked device (including dental exam system 10 and networked devices 405) may comprise a server, personal computer, mobile device (for example, notebook computer, tablet computer, netbook computer, personal digital assistant (PDA), video game device, GPS locator device, cellular telephone, Smartphone, or other mobile device), a television with one or more processors embedded therein and/or coupled thereto, or other appropriate technology that includes or is coupled to a web browser or other application for communicating via the network 402.

In certain examples, the dental exam system 10 is also capable of receiving information from one or more networked devices 405, through network 402, for example from dental professional.

In an example embodiment, the dental exam system 10 has one or more processors embedded therein and/or coupled thereto for example in the electronic mobile device component, or other appropriate technology that can communicate via an electronic, magnetic, or radio frequency field between the dental exam system 10 and another device. In an example embodiment, the dental exam system 10 has processing capabilities, such as storage capacity/memory and one or more applications (not illustrated) that can perform a particular function. In example embodiments, the dental exam system 10 includes a network controller that may be capable of sending and receiving data, performing authentication and ciphering functions, and directing how the dental exam system 10 will listen for and send transmissions from networked devices 405.

In embodiments, the handheld device may be coupled to a video display device, such as a high-definition multimedia interface (HDMI) capable video display device coupled to the handheld computing device, wherein the processor of the handheld computing device is configured to display video on the video display device. In some examples, the handheld computing device includes an integrated video screen, which can display the same or different content than the video display device coupled thereto. For example, the handheld computing device may display video of the subject, while the video display device may display video of another party to the teledentistry session. In some embodiments, the handheld computing device includes application software with executable instructions for conducting a teledentistry session. In some embodiments, the system further includes a speaker coupled to the HDMI capable video display device. In some embodiments, the handheld computing device includes application software with executable instructions for accessing the speaker coupled to the HDMI capable video display device. In some embodiments, the handheld computing device comprises computer executable instructions for: transmitting and receiving video communication from a network; transmitting and receiving audio communication from the network; transmitting video communication received from the network in HDMI format to a HDMI capable video display device; and transmitting an audio communication from the network in HDMI format to the HDMI capable video display device.

An example dental exam system 10 may comprise a memory element (not shown), which can exist within a removable smart chip or a secure digital ("SD") card or which can be embedded within a fixed chip on the dental exam system 10. In certain example embodiments, Subscriber Identity Component ("SIM") cards may be used. In various embodiments, the memory element may allow a software application resident on the dental exam system 10.

In an example, the dental exam system 10 includes a processor. A processor can exist within a removable smart chip or can be embedded within a fixed chip on the dental exam system 10. The application host processor may comprise applications running thereon which perform the functionality described herein.

Figure 5:
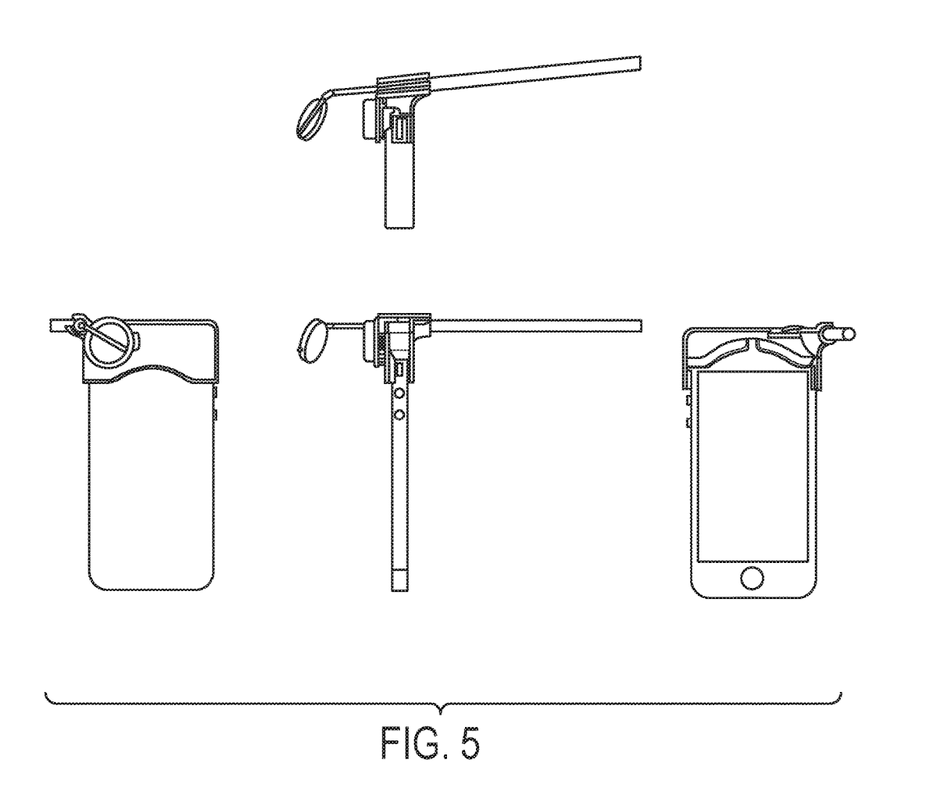
FIGS. 5 and 6 are additional views of exemplary dental exam systems including a dental exam tool, in accordance with embodiments herein.
Figure 6:
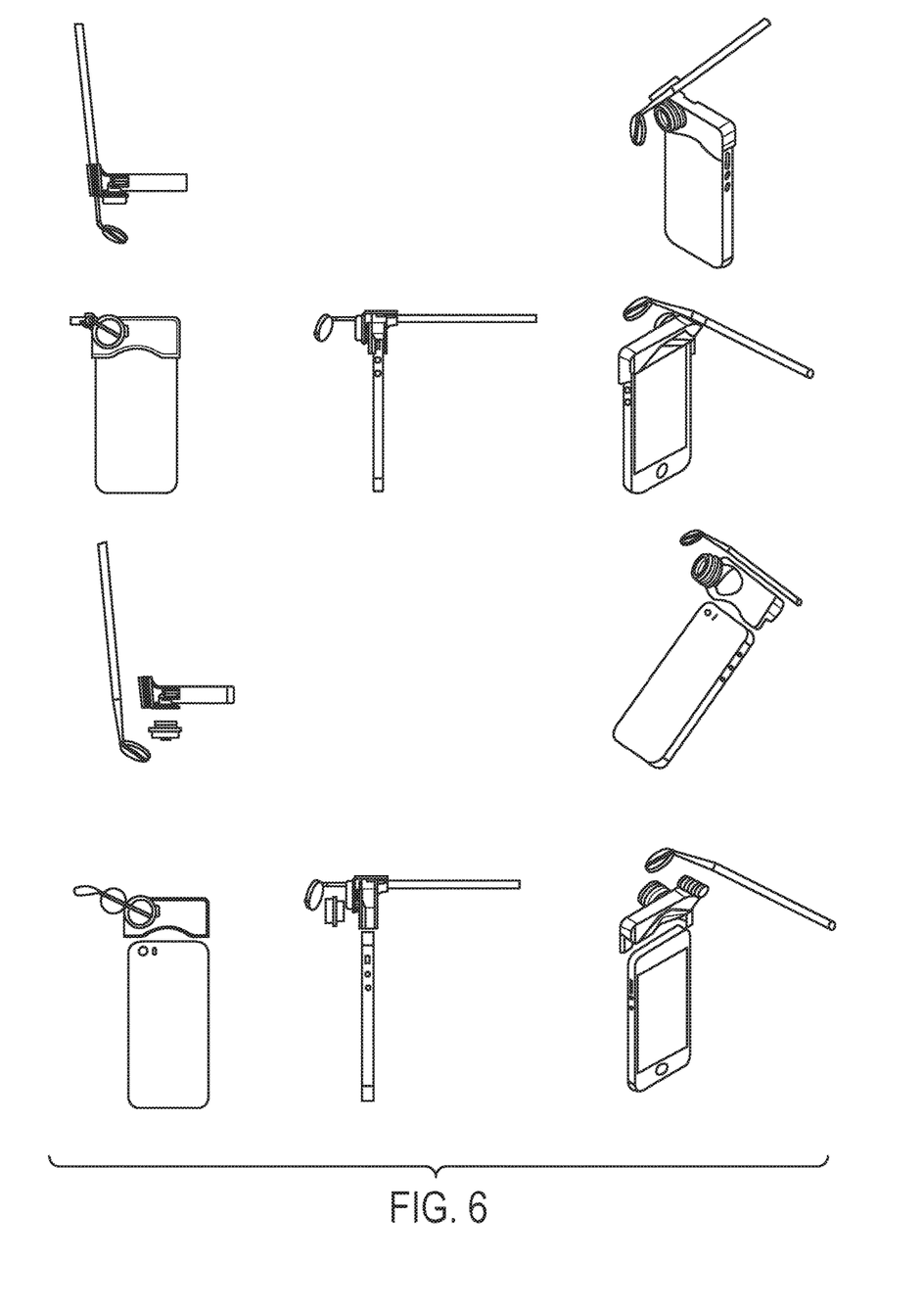

FIGS. 5 and 6 show various images of a mobile dental exam system, in accordance with embodiments herein.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

The invention claimed is:

1. A dental exam tool for attaching to a mobile electronic device, comprising:
   a coupling element that securely and removably couples to a body portion of the mobile electronic device, wherein the coupling element includes an aperture for a camera lens on the body portion of the mobile electronic device; and
   a dental mirror retention element coupled to the coupling element, wherein the dental mirror retention element positions a reflective portion of the dental mirror in front of the camera lens of the mobile electronic device.

2. The dental exam tool of claim 1, wherein the coupling element and the dental mirror retention element are a unitary body.

3. The dental exam tool of claim 1, wherein the dental exam tool is formed from plastic.

4. The dental exam tool of claim 3, wherein the plastic is autoclavable.

5. The dental exam tool of claim 1, wherein the dental mirror retention element is configured to retain a dental mirror with a substantial cylindrical shaft.

6. The dental exam tool of claim 1, wherein the mobile electronic device comprises a cell phone, a smart phone, or a tablet.

7. The dental exam tool of claim 1, wherein the dental coupling element comprises an aperture for a light source of the mobile electronic device.

8. The dental exam tool of claim 1, further comprising a lensing system that removably couples to the dental exam tool.

9. A dental exam system, comprising:
   a dental exam tool for attaching to a mobile electronic device, comprising:
      a coupling element that securely and removably couples to the mobile electronic device; and
      a dental mirror retention element coupled to the coupling element;
   a dental mirror; and
   a mobile electronic device, comprising a camera, wherein the mobile electronic device is capable of capturing still images and/or video from the camera and storing and/or transmitting the images and/or video captured.

10. The dental exam system of claim 9, wherein the coupling element includes an aperture for a camera lens on the body portion of the mobile electronic device.

11. The dental exam system of claim 9, wherein the dental mirror retention element positions a reflective portion of the dental mirror in front of the camera lens of the mobile electronic device.

12. The dental exam system of claim 9, wherein the mobile electronic device comprises a smart phone.

13. The dental exam system of claim 9, wherein the coupling element and the dental mirror retention element are a unitary body.

14. The dental exam system of claim 9, wherein the dental exam tool is formed from plastic.

15. The dental exam system of claim 14, wherein the plastic is autoclavable.

16. The dental exam system of claim 9, wherein the dental mirror retention element is configured to retain a dental mirror with a substantial cylindrical shaft.

17. The dental exam system of claim 9, wherein the mobile electronic device comprises a cell phone, a smart phone, or a tablet.

18. The dental exam system of claim 9, wherein the mobile electronic device is in electronic communication with a third party computing device.

19. The dental exam system of claim 9, wherein the coupling element comprises an aperture for a light source of the mobile electronic device.

20. The dental exam system of claim 9, further comprising a lensing system that removably couples to the dental exam tool.

\* \* \* \* \*